United States Patent [19]
Ogle et al.

[11] Patent Number: 6,165,785
[45] Date of Patent: *Dec. 26, 2000

[54] BONE MARROW CULTURES FOR DEVELOPING SUPPRESSOR AND STIMULATOR CELLS FOR RESEARCH AND THERAPEUTIC APPLICATIONS

[75] Inventors: Cora K. Ogle; John F. Valente; J. Wesley Alexander, all of Cincinnatti, Ohio

[73] Assignees: University of Cincinnati, Cincinnati, Ohio; Shriners Hospitals for Children, Tampa, Fla.

[*] Notice: This patent issued on a continued prosecution application filed under 37 CFR 1.53(d), and is subject to the twenty year patent term provisions of 35 U.S.C. 154(a)(2).

[21] Appl. No.: 09/178,045

[22] Filed: Oct. 23, 1998

Related U.S. Application Data

[63] Continuation of application No. 08/862,533, May 23, 1997, abandoned
[60] Provisional application No. 60/018,247, May 24, 1996.
[51] Int. Cl.[7] .......................... A61K 35/18; A61K 35/26; A61K 35/28
[52] U.S. Cl. ...................... 435/347; 424/93.3; 424/93.7; 424/93.71; 435/2; 435/372; 435/373; 435/384; 435/385; 435/386
[58] Field of Search .................................. 424/93.3, 93.7, 424/93.71; 435/2, 347, 372, 373, 384, 385, 386

[56] References Cited

U.S. PATENT DOCUMENTS

| | | | |
|---|---|---|---|
| 5,399,493 | 3/1995 | Emerson et al. | 435/456 |
| 5,486,359 | 1/1996 | Caplan et al. | 424/93.7 |
| 5,514,364 | 5/1996 | Ilstad | 424/1.49 |
| 5,597,563 | 1/1997 | Beschorner | 424/93.7 |

OTHER PUBLICATIONS

Verbanac, K.M., et al., A role of Transforming growth factor–beta in the veto mechanism in transplant tolerance. Transplantation. 57(6):893–900, Mar. 1994.
Gamelli, R.L., et al., Marrow granulocyte–macrophage progenitor cell response to burn injury as modified by endoxtoxin and indomethacin. J. Trauma 37(3):339–346, 1994.
J. Thomas, et al., Transplantation, 1987, vol. 43, No. 3, pp. 332–338.
Gerhard Opelz, et al., The Lancet, Jun. 6, 1981, pp. 1223–1225.
R.L. Powles, et al., The Lancet, Feb. 16, 1980, pp. 327–329.
Norma K.C. Ramsay, The New England Journal of Medicine, Feb. 18, 1982, vol. 306, No. 7, pp. 392–397.
Shixin Qin, et al., The Journal of Experimental Medicine, Mar. 1989, vol. 169, pp. 779–794.

Megan Sykes et al., Immunology Today, 1988, vol. 9, No. 1, pp. 23–27.
Yedida Sharabi et al., The Journal of Experimental Medicine, Feb. 1989, vol. 169, pp. 493–502.
Jon N. Beresford, B.Sc., Ph.D., Basic Science and Pathology, Mar. 1989 No. 240, pp. 270–280.
Kenneth Dorshkind, Annu. Rev. Immunol, 1990, pp. 111–137.
Joel S. Greenberger, Critical Review in Oncology/Hematology, 1991; 11; pp. 65–84.
Keiji Ono, M.D. et al., Journal of Thoracic and Cardiovascular Surgery, vol. 57, No. 2, Feb. 1969, pp. 225–229.
Cora K. Ogle et al., Inflammation, 1994, vol. 18, No. 2, pp. 175–185.
Hans Wigzell, M.D. et al., The Journal of Experimental Medicine, Aug. 27, 1968, pp. 23–36.
L.J. Wysocki et al., Proc. Natl. Acad. Sci. USA, Jun. 1978, vol. 75, No. 6 pp. 2844–2848.
Christa E. Muller–Sieburg, et al., Cell, Feb. 28, 1986, vol. 44, pp. 653–662.
Adrian P. Gee, et al., Journal of the National Cancer Institute,, Apr. 6, 1988, vol. 80, No. 3, pp. 154–159.
James D. Griffin et al., Blood, Apr. 1984, vol. 63, No. 4 pp. 904–911.
Gabriele E. Schrempf–Decker et al., Journal of Immunological Methods, 32 (1980) pp. 285–296.
Michael G. Mage et al., Journal of Immunological Methods, 15 (1977) pp. 47–56.
Yoshiaki Sonoda et al., Proc. Natl. Acad. Sci. USA, vol. 85, Jun. 1988 pp. 4360–4364.
Amin Tjota et al., Stromal Cells Derived from Spleen or Bone Marrow Support the Proliferation of Rat Natural Killer Cells Long–Term Culture, (43453), P.S.E.B.M. 1992, vol. 200.
Hector Mayani et al., Blood, vol. 81, No. 12, Jun. 15, 1993, pp. 2352–3258.
Sigma Chemical Company, Biochemical Organic Compouns for Research and Diagnostic Reagents, 1992.
Akihisa Kanamaru et al., Augmentation of Erythroid Burst Formation by the Addition of Thymocytes and Other Myelo–Lymphoid Cells, Jounal of Cellular Physiology, 104: 187–197 (1980).

*Primary Examiner*—David Saunders
*Assistant Examiner*—Mary Beth Tung
*Attorney, Agent, or Firm*—Dinsmore & Shohl LLP

[57] ABSTRACT

A method of treatment using immune system suppressor cells and immune system stimulator cells comprises providing stem cells; combining the stem cells with lymphoid-derived cells to produce a co-culture; adding lipopolysaccharide and a factor selected from the group consisting of granulocyte macrophage-colony stimulating factor, macrophage colony stimulating factor, granulocyte-colony stimulating factor and mixtures thereof to the co-culture; obtaining immune system suppressor cells and immune system stimulator cells from the co-culture; and introducing and the cells into a host.

20 Claims, No Drawings

BONE MARROW CULTURES FOR DEVELOPING SUPPRESSOR AND STIMULATOR CELLS FOR RESEARCH AND THERAPEUTIC APPLICATIONS

CROSS REFERENCE TO RELATED APPLICATIONS

This is a continuation of U.S. patent application Ser. No. 08/862,533, now abandoned filed May 23, 1997, which claims priority to U.S. Provisional Pat. Appl. Ser. No. 60/018,247, filed May 24, 1996, both of which are hereby incorporated by reference in their entireties.

STATEMENT OF FEDERALLY SPONSORED RESEARCH

The research underlying this invention has been supported by one or more of the following grants: NIH 5R01 AI12936, NIH 2R01 HL38479, and Shriners Burn Institute Grant 15852.

TECHNICAL FIELD

Previous experimental models have demonstrated the beneficial effects of donor specific blood, bone marrow or spleen cell transfusions and attributed the allograft survival advantage to a variety of cellular candidates, including veto-like cells. See, e.g., *Transplantation* 43:4332 (1987). These models require intrathymic injections in immature recipients, bone marrow ablation, or the use of antilymphocyte serum ("AIS"), in most instances administered prior to transplantation. These restrictions along with the modest effects of bone-marrow transfusion in prospective human trials have limited the clinical application of these methods. In the present invention, the use of donor specific transfusions ("DST") using these cells can achieve better results to other models.

While bone marrow cultured alone is known to generate natural immunosuppressant cells, the infusion of co-culture cells is substantially more effective in prolonging allograft survival. This is especially so when GM-CSF (granulocyte macrophage-colony stimulating factor) and LPS (lipopolysaccharide) are part of the culture conditions. It appears that the suppressor cell activity derived from this co-culture is not donor strain-specific (as third party MLRs (mixed lymphocyte reactions) are equally suppressed). Furthermore, its generation is not dependent on donor specific splenocytes, given the equal to greater graft survival seen with allogeneic (ACI marrow plus Lewis spleen) co-culture infusion.

Factors, such as GM-CSF and LPS are found to induce maturation of bone marrow cultures and generate natural suppressor cells. GM-CSF can enhance the effect of splenic cells on allograft survival. Indeed, GM-CSF has numerous other functions including the expansion, stimulation and development of monocyte populations. The present invention combines these two cell sources and produces a co-culture using both LPS and GM-CSF to optimize suppressor cell generation and function. These cells can be subsequently administered as a form of pre-transplant or post-transplant DST. The present invention generates highly potent suppressor cells which, when given as a DST on the day prior to transplants, may result in a marked prolongation of allograft survival. The present invention also generates highly potent immune system stimulatory cells.

BACKGROUND OF THE INVENTION

Improved allograft survival, occasionally leading to a state of stable transplant tolerance in immunologically mature mammalian systems is achievable by a variety of methods, usually including the use of antilymphocyte antibody preparations and some form of donor cell infusion. Models vary with respect to type of allograft and the timing/route of drug and donor cell administration but many combinations have proved successful. Despite these advances, the clinical application of many of these methods is hampered by the lack of consistent and reliable results in higher primates and man, along with the realities of technical, logistical and chronological limitations inherent in human transplantation. There is, therefore, further need to examine options in the transfusion associated induction of improved allograft survival in solid organ transplantation.

Certain factors have not been fully addressed. First, the avoidance of intensive immunosuppression to limit the incidence of opportunistic infection and tumor formation makes a protocol that avoids use of potent antibody preparations desirable. Second, the enrichment of an antigen/cell source allowing sufficient supply for the multiple recipients of organs from a single cadaveric donor is important. Lastly, the application of an in vitro culture method to enrich immunomodulatory cells could allow for the use of important cytokines and other agents not easily tolerated in-vivo.

The use of either donor blood, bone marrow cells or splenocytes has proved most successful in the induction of prolonged graft survival. In some of these models, the generation of a suppressor-type cell appears to be operative. In other work, the generation of potent suppressor cell populations has been achieved by in-vitro culture of bone marrow with the use of stimulators, especially lipopolysaccharide (LPS). The administration of granulocyte macrophage-colony stimulating factor (GM-CSF) or granulocyte colony stimulating factor ("G-CSF") to donors of bone marrow DST enhances allograft survival. Furthermore, GM-CSF is known to activate marrow-derived natural suppressor cell function. The fractionation of both cell cultures and transplant cellular sources can isolate and enrich subpopulations of cells that retain the properties of suppressor cell function and equally prolong allograft survival.

Transplantation

A major goal in solid organ transplantation is the permanent engraftment of the donor organ without a graft rejection immune response generated by the recipient, while preserving the immunocompetence of the recipient against other foreign antigens. Typically, in order to prevent host rejection responses, nonspecific immunosuppressive agents such as cyclosporine, methotrexate, steroids and FK506 are used. These agents must be administered on a daily basis and if stopped, graft rejection usually results. However, a major problem in using nonspecific immunosuppressive agents is that they function by suppressing all aspects of the immune response, thereby greatly increasing a recipient's susceptibility to infections and other diseases, including cancer.

Furthermore, despite the use of immunosuppressive agents, graft rejection still remains a major source of morbidity and mortality in human organ transplantation. Most human transplants fail within 10 years without permanent graft acceptance. Only 50% of heart transplants survive five years and 20% of cadaveric kidney transplants survive 10 years. (See Opelz et al., 1981, Lancet 1:1223; Gjertson, 1992, UCLA Tissue Typing Laboratory, p. 225; Powles, 1980, Lancet, p. 327; Ramsay, 1982, New Engl. J. Med., p. 392). It would therefore be a major advance if tolerance to the donor cells can be induced in the recipient.

The only known clinical condition in which complete systemic donor-specific transplantation tolerance occurs is when chimerism is created through bone marrow transplantation. (See Qin et al., 1989, J Exp Med. 169:779; Sykes et al., 1988, Immunol. Today 9:23; Sharabi et al., 1989, J. Exp. Med. 169:493). This has been achieved in neonatal and adult animal models as well as in humans by total lymphoid irradiation of a recipient followed by bone marrow transplantation with donor cells. The success rate of allogeneic bone marrow transplantation is, in large part, dependent on the ability to closely match the major histocompatibility complex ("MHC") of the donor cells with that of the recipient cells to minimize the antigenic differences between the donor and the recipient, thereby reducing the frequency of host-versus-graft responses and graft-versus-host disease ("GVHD"). In fact, MHC matching is essential, only a one or two antigen mismatch is acceptable because GVHD is very severe in cases of greater disparities. In addition, it also requires the appropriate conditioning of the recipient by potential lethal doses of total body irradiation (TBI) or cytotoxic drugs.

The MHC is a gene complex that encodes a large array of individually unique glycoproteins expressed on the surface of both donor and host cells that are the major targets of transplantation rejection immune responses. In the human, the glycoproteins are referred to as HLA (human leukocyte antigen) antigens. When HLA identity is achieved by matching a patient with a family member such as a sibling, the probability of a successful outcome is relatively high, although GVHD is still not completely eliminated. However, when allogeneic bone marrow transplantation is performed between two MHC-mismatched individuals of the same species, common complications involve failure of engraftment, poor immunocompetence and a high incidence of GVHD. Unfortunately, only about 20% of all potential candidates for bone marrow transplantation have a suitable family member match.

The field of bone marrow transplantation was developed originally to treat bone marrow-derived cancers. It is believed by those skilled in the art even today that lethal conditioning of a human recipient is required to achieve successful engraftment of donor bone marrow cells in the recipient. In fact, prior to the present invention, current conventional bone marrow transplantation has exclusively relied upon lethal conditioning approaches to achieve donor bone marrow engraftment. The requirement for lethal irradiation of the host which renders it totally immunocompetent poses a significant limitation to the potential clinical application of bone marrow transplantation to a variety of disease conditions, including solid organ or cellular transplantation, sickle cell anemia, thalassemia and aplastic anemia.

Immunosuppressive agents are also extensively used following organ transplantation for the prevention of rejection episodes. In particular, cyclosporine, a potent immunosuppressive agent, prolongs the survival of allogeneic transplants involving skin, heart, kidney, pancreas, bone marrow, small intestine, and lung in animals. Cyclosporine has been demonstrated to suppress some humoral immunity and to a greater extent, cell mediated reactions such as allograft rejection, delayed hypersensitivity, experimental allergic encephalomyelitis, Freund's adjuvant arthritis, and graft versus host disease in many animal species for a variety of organs.

U.S. Pat. No. 5,514,364, Ildstad, issued May 7, 1996, discloses non-lethal methods of conditioning a recipient for bone marrow transplantation. In particular, it relates to the use of sub-lethal doses of total body irradiation, cell type-specific antibodies, especially antibodies directed to bone marrow stromal cell markers, cytotoxic drugs, or a combination thereof. The methods of the invention have a wide range of applications, including, but not limited to, the conditioning of an individual for hematopoietic reconstitution by bone marrow transplantation for the treatment of hematological malignancies, hematological disorders, auto immunity, infectious diseases such as acquired immunodeficiency syndrome, and the engraftment of bone marrow cells to induce tolerance for solid organ, tissue and cellular transplantation.

U.S. Pat. No. 5,486,359, Caplan et al., issued Jan. 23, 1996, discloses isolated human mesenchymal stem cells which can differentiate into more than one tissue type (e.g., bone, cartilage, muscle or marrow stroma), a method for isolating, purifying, and culturally expanding human mesenchymal stem cells (i.e., "mesenchymal stem cells" or "hMSCs"), and characterization of and uses, particularly research reagent, diagnostic and therapeutic uses for such cells. The stem cells can be culture expanded without differentiating.

None of these references individually or collectively teach or suggest the present invention.

SUMMARY OF THE INVENTION

The present invention relates to methods of producing distinct populations of cells capable of immune suppressor and stimulatory action. Specifically, the methods relate to a combination of splenocyte and bone marrow cells, co-cultured with LPS and GM-CSF, which induce two cell subpopulations. One cell subpopulation has an immune system suppressory function capable of prolonging allograft survival when infused as a donor specific blood transfusions ("DST") with a low dose, eight day course of cyclosporine ("CSA"). Another cell subpopulation has an immune system stimulatory function capable of stimulating the immune system when infused as a DST.

Previous experimental models have demonstrated the beneficial effects of donor specific blood, bone marrow or spleen cell transfusions and attributed the allograft survival advantage to a variety of cellular candidates, including veto-like cells. See, e.g., *Transplantation* 43:4332 (1987). In the present invention, the use of donor specific transfusions ("DST") using these cells can achieve better results to other models.

The present invention combines these two cell sources and produces a co-culture using both lipopolysaccharide ("LPS") and granulocyte macrophage-colony stimulating factor ("GM-CSF") to optimize suppressor cell generation and function. These cells can be subsequently administered as a form of pre-transplant DST. The present invention generates highly potent suppressor cells which, when given as a DST on the day prior to transplants, may result in a marked prolongation of allograft survival. The present invention also generates highly potent stimulatory cells.

The method of their isolation comprises the steps of providing a tissue specimen containing stem cells, adding cells from the tissue specimen to a medium which contains factors that stimulate stem cell growth and allows, when cultured, for the selective differentiation of the stem cells into two distinct subpopulations of cells, one with an immune suppression function and one with an immune stimulation function. Any suitable cell sorting method may then separate the cells as known in the art.

In another aspect, the present invention relates to a medium for the selective differentiation of the stem cells into two distinct subpopulations of cells, one with an immune suppression function and one with an immune stimulation function, wherein the medium comprises cells and/or factors that stimulate stem cell differentiation.

In a further aspect, the present invention relates to a kit for differentiating stem cells from a tissue specimen. The kit comprises a medium containing factors and/or cells which stimulate the differentiation of the stem cells into two distinct subpopulations of cells, one with an immune suppression function and one with an immune stimulation function.

In an additional aspect, the present invention is directed to various methods of utilizing the differentiated stem cells produced by the present invention for therapeutic and/or diagnostic purposes. For example, the differentiated stem cells may find use in: (1) regenerating tissues which have been damaged through acute injury, abnormal genetic expression or acquired disease; (2) treating a host with damaged tissue by removal of small aliquots of bone marrow, differentiating them in vitro, isolating the desired subpopulation of differentiated cells and reintroducing the differentiated cells back into the host (3) detecting and evaluating growth factors relevant to the immune system; (4) detecting and evaluating inhibitory factors which modulate the immune system.

The present invention also relates to methods of inducing at least partial tolerance to an antigen comprising the steps of administering to the recipient animal a tolerogenic amount of a dendritic cell population, and administering to the recipient animal a tolerogenic amount of a suppressor cell population, substantially contemporaneously with the dendritic cell population. The antigen may be an alloantigen, autoantigen, or xenoantigen.

DETAILED DESCRIPTION OF THE INVENTION

The present invention relates to methods of producing distinct populations of cells capable of immune suppressor and stimulatory action. Specifically, the methods relate to a combination of splenocyte and bone marrow cells, co-cultured with LPS and GM-CSF, which induce two cell subpopulations. One cell subpopulation has an immune system suppressory function capable of prolonging allograft survival when infused as a donor specific blood transfusions ("DST") with a low dose, eight day course of cyclosporine ("CSA"). Another cell subpopulation has an immune system stimulatory function capable of stimulating the immune system when infused as a DST.

The present invention combines these two cell sources and produces a co-culture using both lipopolysaccharide ("LPS") and granulocyte macrophage-colony stimulating factor ("GM-CSF") or granulocyte colony stimulating factor ("G-CSF") to optimize suppressor cell generation and function. These cells can be subsequently administered as a form of pre-transplant DST. The present invention generates highly potent suppressor cells which, when given as a DST on the day prior to transplants, may result in a marked prolongation of allograft survival. The present invention also generates highly potent stimulatory cells.

The method of their isolation comprises the steps of providing a tissue specimen containing stem cells, adding cells from the tissue specimen to a medium which contains factors that stimulate stem cell growth and allows, when cultured, for the selective differentiation of the stem cells into two distinct subpopulations of cells, one with an immune suppression function and one with an immune stimulation function. Any suitable cell sorting method may then separate the cells as known in the art.

In another aspect, the present invention relates to a medium for the selective differentiation of the stem cells into two distinct subpopulations of cells, one with an immune suppression function and one with an immune stimulation function, wherein the medium comprises cells and/or factors that stimulate stem cell differentiation.

In a further aspect, the present invention relates to a kit for differentiating stem cells from a tissue specimen. The kit comprises a medium containing factors and/or cells which stimulate the differentiation of the stem cells into two distinct subpopulations of cells, one with an immune suppression function and one with an immune stimulation function.

In an additional aspect, the present invention is directed to various methods of utilizing the differentiated stem cells produced by the present invention for therapeutic and/or diagnostic purposes. For example, the differentiated stem cells may find use in: (1) regenerating tissues which have been damaged through acute injury, abnormal genetic expression or acquired disease; (2) treating a host with damaged tissue by removal of small aliquots of bone marrow, differentiating them in vitro, isolating the desired subpopulation of differentiated cells and reintroducing the differentiated cells back into the host (3) detecting and evaluating growth factors relevant to the immune system; (4) detecting and evaluating inhibitory factors which modulate the immune system; (5) treatment of infections, cancer, and burns in a patient in need of such treatment; (6) treatment of autoimmune diseases, e.g., rheumatoid arthritis; and (7) for pre- or post-transplantation therapy.

Factors, such as GM-CSF and LPS are found to induce maturation of bone marrow cultures and generate natural suppressor cells. GM-CSF can enhance the effect of splenic cells on allograft survival. Indeed, GM-CSF has numerous other functions including the expansion, stimulation and development of monocyte populations. In one embodiment of the present invention, the method combines these two cell sources and produces a co-culture using both LPS and GM-CSF to optimize suppressor cell generation and function. These cells can be subsequently administered as a form of pre- or post-transplant DST utilizing highly potent suppressor cells generated which, when given as a DST on the day prior to transplants, may result in a marked prolongation of allograft survival. The present invention also generates highly potent stimulatory cells that can be subsequently administered as a method of stimulating the immune capability in an immune compromised patient.

While not being bound by theory, it is believed that the action of the splenocytes on the bone marrow cells is likely derived from a secretory product; other embodiments may utilize a culture system where the splenocytes are replaced by other secretory cells. Still other embodiments may utilize a culture system where the splenocytes are replaced by cytokines, cytokine-producing cells, or lymphoid derived cells.

While bone marrow cultured alone is known to generate natural suppressor cells, the infusion of co-culture cells is substantially more effective in prolonging allograft survival. This is especially so when GM-CSF and LPS are part of the culture conditions. It appears that the suppressor cell activity derived from this co-culture is not donor strain-specific (as third party MLRs are equally suppressed). Furthermore, its generation is not dependent on donor specific splenocytes.

Bone marrow is the soft tissue occupying the medullary cavities of long bones, some haversian canals, and spaces between trabeculae of cancellous or spongy bone. Bone marrow is of two types: red, which is found in all bones in early life and in restricted locations in adulthood (i.e., in the spongy bone) and is concerned with the production of blood cells (i.e., hematopoiesis) and hemoglobin (thus, the red color); and yellow, which consists largely of fat cells (thus, the yellow color) and connective tissue.

As a whole, bone marrow is a complex tissue comprising hematopoietic stem cells, red and white blood cells and their precursors, mesenchymal stem cells, stromal cells and their precursors, and a group of cells including fibroblasts, reticulocytes, adipocytes, and endothelial cells which form a connective tissue network called "stroma". Cells from the stroma morphologically regulate the differentiation of hematopoietic cells through direct interaction via cell surface proteins and the secretion of growth factors and are involved in the foundation and support of the bone structure. Studies using animal models have suggested that bone marrow contains "pre-stromal" cells that have the capacity to differentiate into cartilage, bone, and other connective tissue cells. (Beresford, J. N., *Clin. Orthop.*, 240:270 (1989)). Recent evidence indicates that these cells, called pluripotent stromal stem cells or mesenchymal stem cells, have the ability to generate into several different types of cell lines (i.e., osteocytes, chondrocytes, adipocytes, etc.) upon activation. However, the mesenchymal stem cells are present in the tissue in very minute amounts with a wide variety of other cells (i.e., erythrocytes, platelets, neutrophils, lymphocytes, monocytes, eosinophils, basophils, adipocytes, etc.), and, in an inverse relationship with age, they are capable of differentiating into an assortment of connective tissues depending upon the influence of a number of bioactive factors.

The methods of the present invention may use bone marrow cells obtained from iliac crest, femoral, tibiae, spine, rib or other medullary spaces. Alternatively, the methods could use stem cells from other sources of human stem cells, e.g., from embryonic yolk sac, placenta, umbilical cord, fetal and adolescent skin, and blood.

Mesenchymal stem cells are the formative pluripotential blast cells found inter alia in bone marrow, blood, dermis and periosteum that are capable of differentiating into any of the specific types of mesenchymal or connective tissues (i.e., the tissues of the body that support the specialized elements; particularly adipose, osseous, cartilaginous, elastic, and fibrous connective tissues) depending upon various influences from bioactive factors, such as cytokines. In a further embodiment, the bone marrow cells may consist entirely of mesenchymal stem cells.

The hematopoietic microenvironment is primarily composed of hematopoietic cells and stromal cells. Hematopoietic cells include pluripotent uncommitted stem cells and unipotent committed stem cells, and differentiate into macrophages, monocytes, lymphocytes, erythrocytes, platelets, basophils, neutrophils and eosinophils. The stromal cells occupy much space of the bone marrow environment and they include endothelial cells that line the sinusoids, fibroblastic cells such as adventitial reticular cells, perisinusoidal adventitial cells, periarterial adventitial cells, intersinusoidal reticular cells and adipocytes, and macrophages (Dorshkind, *Annu. Rev. Immunol.* 8:111, (1990); Greenberger, *Crit. Rev. Oncology/Hematology* 11:65, (1991)). In another embodiment, the bone marrow cells may comprise hematopoietic cells or stromal cells.

The present invention includes a method of achieving stable engraftment of donor organs or tissues by conditioning a recipient for organ or tissue transplantation with a donor cell preparation containing stem cells conditioned to differentiate into immune system suppressory cells.

In a further embodiment, the stem cell is a cell selected from the group consisting of endothelial cells, adventitial reticular cells, perisinusoidal adventitial cells, periarterial adventitial cells, intersinusoidal reticular cells, adipocytes, macrophages and hematopoietic facilitator cells. In another embodiment, mesenchymal stem cells are used.

The methods of the present invention provide an isolated, homogeneous population of stem cells that are differentiated into cells of distinct subpopulations. Preferably, the stem cells are obtained from bone marrow. Most preferably, the stem cells are obtained from bone marrow of a donor who was previously a recipient of the differentiated cells. Alternatively, the stem cells are obtained from periosteum.

In another embodiment, the present invention provides a composition comprising the stem cells and a culture medium; wherein said culture medium differentiates the said stem cells into two subpopulations of cells.

In another embodiment, the present invention provides a therapeutic composition comprising one of the subpopulations of differentiated stem cells and a pharmaceutically acceptable carrier; wherein said subpopulation of stem cells is present in an amount effective to produce immune system regulation.

Discussion

The suppressor effect may be concentrated by PERCOLL fractionation and further enriched by FACS (fluorescence antibody cell sorter) sorting of the "nonlymphocyte" region of this fraction. In stark contrast to fraction 3, cells isolated in fraction 4 are highly stimulatory. On light microscopy the fraction 3 cells appeared as highly activated foamy macrophages. The FACS signature of this cell population is bland, with few positive markers noted in the active region of fraction 3. Specifically, the cell is not a lymphocyte, showing no staining for CD, CD4, CD8 or the rat pan-T cell clone OX-52. The cells are positive for a rat macrophage antigen marker (clone R2-1A6A) and we found significant staining with the antibody clone OX-33 (marking for CD45RA) in these cells as well. This cell bears little similarity to veto cells, dendritic cells, facilitator cells, progenitor cells, or some of the previously described natural suppressor cells, but appears to be a highly suppressive macrophage derived from the conditions of the co-culture.

Specific data regarding tolerance induction using these cells is not yet available, but individual graft survival can be greatly prolonged. We have found the ACI to Lewis strain combination to be remarkably stringent, with loss of graft function from acute rejection occurring reliably at about 7 days in controls, and at 16 days in animals given DST and CSA. In animals receiving tolerance induction protocols, rejection is still possible, even after 100 days of allograft survival without drug therapy. Furthermore, while the choice of CSA is important for its potentiating effect on the DST of blood protocol, the low dose CSA used in this protocol confers no independent advantage for graft survival.

These findings are of interest given the relative potency of the suppressor cell generated, with PHA and MLR suppression in-vitro or graft survival prolongation in-vivo using a 10–100 fold decrease in cell numbers as compared to previous reports. Similar cells (although less potent) have been described and the general phenomenon of increased effectiveness of fractionated cells is in agreement with previous studies. Donor specific bone marrow transfusion with previous ALS treatment is noted to reduce the number or function of donor-reactive cytotoxic T lymphocytes for the duration of graft survival. A myeloid-derived natural suppressor cell has also been described in human bone marrow, but the effect of GM-CSF or LPS on these cells is not currently known. When those untreated cells are used in in-vitro experiments, they are found to be immunostimulatory at "low" doses ($\leq 4 \times 10^5$ cells added to $1 \times 10^6$ responder cells) and suppressive at higher doses. Cells with potent, nonspecific natural suppressor function are also noted in the circulation of long term renal transplant recipients. Activated macrophages from other sources, such as lung lavage, are known to possess suppressor function, however, macrophages represent a large group of varied circulating and tissue associated effector cells with a bewildering repertoire of secretory products and functions. Different macrophages behave quite differently and accurate comparisons of co-culture derived cells with in-vivo derived cells cannot be made. Furthermore, the specific function of the cell in question can be variable, as both veto activity and natural suppressor activity can be demonstrated by human lymphokine activated cells depending on their concentration in the MLR.

The use of spleen cells in the co-culture is important given the much lower allograft survival noted with pure bone-marrow culture infusion. Since both spleen and marrow are contaminated with peripheral blood white cells, but marrow cells cultured alone failed to enhance allograft survival, it seems likely that a cell or factor(s) secreted by a cell within the spleen is responsible for this added effect. Previous studies using transfused spleen cells show prolongation of graft survival only with intermediate doses of cells and show these spleenderived suppressor cells to be $FcR^+$ non-lymphocytes. Whether the macrophage-like cell noted in fraction 3 is of splenic or marrow origin, whether splenic lymphocytes or other cells provide "help" in the culture, and why recipient specific spleen works as well (or better) than donor specific spleen is currently under study. The effectiveness of syngeneic spleen cells in this model is intriguing. In the past, only donor specific spleen has routinely been used with success (but not in co-culture). Use of recipient specific spleen to condition an organ donor is not easily applied clinically. The fact that the splenic strain is interchangeable in invention is a novel finding.

The improvement in allograft survival seen with co-culture cell infusion is achieved with a clinically ineffective dose of CSA, without ALS, and in a non-irradiated recipient with a mature (adult) and very strong recipient immune system. The possibility of further enhancement of allograft survival with the addition of ALS exists, but the timing of ALS therapy with a day 1 DST may be difficult. In bone marrow DST studies, technique and timing of administration become important as graft vs. host disease, sensitization with hyperacute rejection, and complete loss of the DST effect can all occur. For example, the use of bone-marrow infusion on day 0 with concurrent or subsequent ALS has been shown to cause sensitization rather than improved allograft survival. A number of ALS preparations including monoclonal antibodies (anti-CD3) are known to induce secretion of colony stimulating factors, possibly making administration prior to bone-marrow cell infusion important. Furthermore, the use of ALS after bone marrow cell infusion may alter the cytokine milieu and reduce the effect. Therefore, correlates might be found between the in-vivo and in-vitro timing of GM-CSF induction, cytokine secretion and cell infusion. While removing the need for prolonged, pre-transplant drug therapy and shortening the period between DST administration and transplantation is a significant advance toward clinical applicability, the use of any day—1 protocol is still not always easily applicable to the cadaveric donor situation, especially when co-culture time is considered. Although suppressor cells are shown to be capable of inhibiting proliferation of actively dividing, prestimulated lymphocytes, whether such suppressions of an MLR or post-transplant in vivo sensitization are possible remains to be studied. The culture method described could however, obviate the need for marrow cryopreservation in protocols using the transfusion later in the post-transplant course, while enhancing the effect of the administered cells. Furthermore, suppressor cells may be obtainable with shorter culture times, as marrow cells cultured only four days note inhibition of splenocyte proliferation. DST given only 12 hours pre-transplant and in many models multiple DSTs after transplants are also effective strategies allowing immediate clinical applicability of co-cultures maintained for shorter periods of time.

The cytokine milieu developed within the co-culture is undoubtedly significant in the development and therefore function of the suppressor cells created. The use of LPS in bone marrow culture induces interferon ("IFN") dependent production of nitric oxide, responsible for suppressor cell functions but other cytokines are likely involved in the development of the suppressor cell as well. We did note a high level of IFN present initially in our culture supernatant. As this mediator is shown to be important in suppressor cell function, activation, and the restoration of activation after impairment of suppressor function by glucocorticoids, it may be an important initial signal at the start of the culture conditions. The levels of TGFβ (transforming growth factor beta) are noted to rise over time, a consistent finding both with the development of natural suppressor cells in the culture and with their subsequent actions in prolonging the survival of allografts. In addition, IL-4 (interleukin-4) may be important for suppressor cell development or function (or as a consequence thereof) as concentrations are noted to progressively rise over the 7-day course of co-culture. Other cytokines, including IL-6 (interleukin-6) may play an important role in the maintenance of suppressor function as well. In our study, IL-6 (interleukin-6) is low initially, peaked at day four, and remained relatively high on day seven. Low levels of TNF (tumor necrosis factor) are detected for all culture times. In other studies, TNFα (tumor necrosis factor alpha) has been shown to inhibit the function and division of human marrow progenitor cells in vitro. We have not measured cell-associated TNF in this model, however. As anticipated, significant elevations in $PGE_2$ (prostaglandin $E_2$) levels are noted over time with peak levels at day seven. This finding is consistent since $PGE_2$ can be immunosuppressive and is a secretory product of activated suppressor cells. Overall, the culture supernatants show an initial pro-inflammatory profile over the first four days, converting around that time to include a different class of regulatory cytokines associated with suppressor cell function.

The effect of co-culture supernatant on the MLR response is of interest, especially since inhibition is not seen until day four and early supernatant (day 0) is stimulatory, suggesting that the cells placed in culture are initially primed to be pro-inflammatory. However, suppression of peripheral blood monocyte response to PHA by normal alveolar macrophages is thought to be dependent upon cell-cell contact. Those cells are obtained from healthy subjects, used fresh, and not cultured with stimulatory factors. Several other studies have demonstrated and initially characterized potent, soluble, suppressive factors secreted by marrow and spleen derived suppressor cells. Clinically important soluble factors have been described from other cell sources as well. The possibility that veto and suppressor mechanisms are not due to separate cells, but represent a spectrum of functions has some support in the literature. It seems likely that cytokines, like those noted in the co-culture supernatants (PGE$_2$, TGFβ and others) are responsible for at least a part of the MLR suppression, and may represent the soluble factors noted when highly activated suppressor cells are studied. Whether a lower state of activation or a reduced effective concentration of these cells could result in veto-like functions remains to be studied.

The current model shows a macrophage, derived from seven days of LPS and GM-CSF stimulated co-culture of bone marrow cells and splenocytes, with the ability to inhibit both in-vitro and in-vivo immune responsiveness, resulting in significant prolongation of rat cardiac allograft survival. This cell demonstrates natural suppressor functions at low doses in vitro (a single fraction three macrophage per 200 responder splenocytes) and remarkable potency when infused in a transplant model (<1×10$^7$ whole culture cells/kg). These results are achieved with low dose (clinically ineffective) CSA as the only immunosuppressive agent. Further purification and characterization of these cells and determination of their mode of action should lead to a better understanding of the mechanisms of their suppressive effect and immune tolerance in general.

Bone Marrow Preparation. Whole, unfractionated bone marrow is typically obtained from rib or long bones by flushing with Hank's Balanced Salt Solution ("HBSS"), or vertebral body bone marrow obtained by crushing with a bone rongeurs and elution with buffer solution, is filtered through nylon mesh and the viability assessed by trypan blue exclusion using a hemocytometer. The cells are collected by centrifugation at 1400 rpm for five minutes and then lysed with 25 mL of sterile, distilled water followed immediately by 25 mL of double strength HBSS. Cells are then recollected by centrifugation and pooled into one conical tube using a horizontal pipetting technique to exclude agglutinated material. Cells are resuspended in Roswell Park Memorial Institute Media ("RPMI") at a concentration of 1–2×10$^6$ large mononuclear cells /mL and incubated at 37° C. in 5% CO2 for one hour (to adhere cells). The nonadherent cells are collected and washed in HBSS and the viability rechecked. Cells are stored at 4° C. until used.

Splenocyte Preparation. Typically, splenic tissue is cut into small (approximately 0.5–1 gm) pieces and crushed using any convenient method (between glass slides and using a scraping technique with a sterile disposable blade), and collected in HBSS. The tissue is filtered through nylon mesh and collected by centrifugation. The cells are pooled and resuspended in 15 mL of HBSS, beneath which is layered 7.5 mL of FICOLL-HYPAQUE. This gradient is centrifuged at 1000 rpm for 45 minutes (no brake) and the interface cells collected and pooled. The pellet and solution are discarded. The pooled cells are washed three times in HBSS and resuspended in RPMI, and viability and cell counts checked. Cells are stored at 4° C. until used.

Culture Set-Up. Splenocytes and bone marrow cells are resuspended in RPMI or similar medium to a concentration of 2×10$^6$ cells/mL and added together in equal amounts. The media is supplemented with the appropriate growth factor or stimulant and incubated at 37° C. in 5% CO$_2$ (minimum but not to exceed 10%) at a concentration of 3.3×10$^5$ cells/square cm floor surface. Cultures are maintained using standard humidity, for at least four days (and up to 14 days) undisturbed and unshaken.

Supplemental Factors: Specific supplementation with colony stimulating factors is necessary. The current technique utilizes species specific granulocyte macrophage-colony stimulating factor (GM-CSF). Where species specific factor is unavailable (i.e., the rat) murine GM-CSF is used and a concentration of 100 units/mL is added at the start of the culture. Additional agents for the stimulation and maturation of cells are added. The current model employs lipopolysaccharide (LPS or bacterial endotoxin) obtained from *E coli* and added at 1 μg/mL at the start of the culture. Additional growth/factors that may be used in addition or in place of GM-CSF include macrophage colony stimulating factor ("M-CSF"), granulocyte-colony stimulating factor ("G-CSF") and the FLT3 ligand. Additional stimulating factors that may be added or used in place of LPS include interluekin-6, interleukin-4, tumor necrosis factor alpha ("TNFα"), and transforming growth factor beta ("TGFβ"). Again, all factors used are species specific unless unavailable, in which case either murine or human factors can be employed.

Cell Harvest. Typically, cells are harvested and pooled by first obtaining nonadherent cells and rinsing the culture container and collecting the cells and washes in separate tubes. Following centrifugation, supernatants may be saved or frozen for analysis. The cells are resuspended and counted and their viability checked using trypan blue exclusion. Cells may be used unfractionated or following a number of fractionation techniques. The current method employs the use of unfractionated cells resuspended in sterile, pH-balanced medium. For fractionation, a discontinuous PERCOLL gradient is used with a 100%, 70%, 60%, 50%, 40% and 0% stepwise dilution. The cells are suspended in 100% PERCOLL and equal volumes of diluted PERCOLL are layered sequentially above the cells. The gradient is harvested after centrifugation at 1000 g (2300 rpm) for 60 minutes. Cells are obtained separately at each interface, counted, and the viability checked. The individual subfractions may be used alone or in combinations for research or therapeutic purposes.

The methods of the present invention may be used to enhance allograft survival in a transplant patient and also to obtain specific populations of cells with stimulatory or suppressive capacities using fractionation by the PERCOLL method, FACS sorting or other suitable cell separation method as known in the art. These subpopulations may be used in in vitro testing using lymphocyte proliferation assays. This technique can provide cell cultures in animal and human systems for use in specific clinical/medical applications involving malignancy or inflammation. Whole cultures or derived subpopulations can be applied (by standard or intraportal venous transfusion techniques) for the treatment of immune system dysfunction, infection prevention and modulation of systemic inflammation in patients with thermal injury, infection, multiple trauma, and sepsis. The transfusion of donor-specific cell cultures can be used for the prevention or reduction in organ transplant rejection. Subpopulations of culture cells will be useful in the treatment of autoimmune disorders and malignancies.

The use of different growth factors and stimulatory agents/cytokines can be tailored to the specific therapeutic advantage (see above), the use of these same or other growth factors may mobilize marrow cells into donor peripheral blood as a source of culture cells. The use of growth factors of stimulatory agents to enhance the effects of the cultured cells before, during or after administration is also a direct extension of this work.

Co-culture Technique: Fresh spleens and lower extremity long bones are harvested aseptically and kept on ice in Hank's balanced salt solution (HBSS, Gibco Life Technologies, Gaithersburg Md.). Spleens are crushed between glass slides and sterile, filtered, splenic tissue is washed in HBSS, centrifuged on a FICOLL-HYPAQUE (HISTOPAQUE 1077, Sigma Diagnostics, St. Louis, Mo.) gradient at 1000 RPM×45 min. and the white cell layer harvested, washed twice, resuspended in Roswell Park Memorial Institute (RPMI) medium (Gibco) with 10% fetal calf serum (FCS) (Hyclone Labs, Logan, UT) and 100 units/mL penicillin, 100 µg/mL streptomycin sulfate, and 0.25 µg/mL amphotericin B (Gibco), to $2\times10^6$ cells/ml. Bone marrow harvests are performed as previously described by Ogle et al., *Inflammation* 18:175 (1994). The marrow cells are resuspended in RPMI+10% FCS, counted and diluted to $1\times10^6$ large, mononuclear cells/ml. Twenty-five mL aliquots are incubated for 60 min. at 37° C. and 5% $CO_2$ in 250 mL, 75 $cm^2$ sterile, vented culture flasks (Costar, Cambridge Mass.). Nonadherent cells are then collected, washed and resuspended to $2\times10^6$ cells/mL. Co-cultures consisted of equal volumes of spleen and marrow cells (total $1\times10^6$ of each cell stock/mL), most with added LPS (1 µg/mL, *E. coli* 055:B5, Sigma Chemical, St. Louis, Mo.) and murine GM-CSF (100 units/mL, R and D Systems, Minneapolis, Minn.) and are incubated for up to seven days at 37° C. and 5% $CO_2$ in 25 ml volumes in 250 mL sterile culture flasks. All cell counts are based on viable cells by trypan blue exclusion. Nonadherent co-culture cells are harvested at predetermined times, washed, resuspended and counted.

Some initial cultures using nonadherent bone marrow only are performed with various combinations of LPS, murine GM-CSF, recombinant human TNFα (100 units/ml, Endogen, Boston Mass.) or unmodified media and harvested at day four or seven and used in mixed lymphocyte and phytohemagglutinin (PHA, Sigma, St. Louis, Mo.) experiments.

Cell Fractionation: Cells are washed twice in HBSS, pelleted in a 15-ml conical tube at 1400 RPM×5 min. and resuspended to 2 ml in PERCOLL (Pharmacia, Uppsala, Sweden) solution (0.95 ml 10× HBSS in 9.05 ml sterile 100% PERCOLL, pH titrated to 7.35) over which are layered 2 ml each of 70%, 60%, 50%, 40% and 0% (plain HBSS) PERCOLL dilutions. After centrifugation at 2800 RPM×30 min., fractions at gradient interfaces are retrieved, washed and resuspended in RPMI with 10% FCS. Fractions (Fr) are labeled sequentially from the 100–70% interface (Fr 1) to the 40–0% interface (Fr 5). The fractionation of untreated bone marrow yielded four fractions (lacking cells at the 50–40% interface), while seven-day co-cultures yielded five fractions. Fraction five contained 97% dead cells, while Frs 1 and 2 contained very few but mostly viable cells (these are submitted for FACS analysis). Fraction 3 contained the majority of total cells (66%) at 95% viability, while Fr 4 contained somewhat fewer cells at similar viability (Frs 3 and 4 are used in further experiments). Subsequent separation of Fr 3 cells is accomplished by sterile, viable cell sorting on an Epics 753 cell sorter (Coulter, Miami Fla.) into subpopulations based on scatter pattern (debris, lymphocyte, and macrophage regions). An average of 60% of cells is lost during sorting. This is attributed to fragility acquired by some cells over time in culture. Macrophage region cells are used in further experiments.

Mixed Lymphocyte Reactions: Spleens are harvested aseptically, crushed, filtered and washed in HBSS, then resuspended in 15 ml HBSS and separated on a FICOLL-HYPAQUE gradient at 1000 RPM×45 min. The white cells are harvested, washed, resuspended in RPMI with 10% FCS and cells incubated with 25 Fg Mitomycin C (Sigma, St. Louis, Mo.)/$2.5\times10^7$cells/mL for 45 minutes at 37° C. and 5% $CO_2$ then washed 3× in RPMI are used as stimulator cells. Responder and stimulator cells are added to standard 96 well culture plates at $2.0\times10^6$ cells/well to which are added titrations of whole co-culture, fr 3, or fr 4 cells or titrated amounts of co-culture supernatant. Cells are pulsed with 0.5 FCi/well of $^3$H-thymidine (1 mCi/mL New England Nuclear, Boston, Mass.) and harvested on day 4. Activity is measured as counts per minute (cpm) with an LS600TA liquid scintillation counter (Beckman, Fullerton, Calif.). All reactions are performed in triplicate and results expressed as mean values.

PHA (phytohemagglutinin) stimulation: Spleens are harvested, washed and separated as for MLR above. White cells resuspended in RPMI with 10% FCS are incubated in triplicate on standard 96 well culture plates with 1 Fg/well PHA. Co-culture and Fr 3 cells are titrated in variable amounts and cpm are measured as for MLRs. All results are expressed as means of triplicate values in both MLR and PHA reactions. The percentage of suppression is calculated using the following formula:

$$\% \text{ suppression}=100\times\{cpm^{test\ cells}\times100/cpm^{control}\}.$$

The % of activation is calculated simply as the multiple of increase over baseline×100.

Antibodies and FACS Analysis: Biotin labeled IgG anti-pan-T (murine clone OX-52), IgG anti CD4 (OX-38), and IgG anti-CD8a (G28) with labeled isotype $IgG_{2a}$; biotin labeled IgG anti-CD45RA (OX-33) with labeled isotype $IgG_1$; biotin labeled IgA anti-rat CD11b (wt.5) with labeled isotype IgA;phycoerytherin (PE) labeled IgG anti-rat RT1b (anti MHC-II, clone OX-6) and IgG anti-Thy 1.1 (CD90, clone OX-7) with labeled isotype, biotin labeled IgG anti-TCRαβ (R73) with biotin and PE labeled $IgG_1$ isotypes; and PE labeled IgG anti-CD3 (G4.18) with labeled isotype $IgG_3$ are purchased from Pharimgen (San Diego, Calif.). Fluorescein isothiocyanate (FITC) labeled IgM anti-PMN and FITC labeled IgM anti-PMN/Mac (R2-1A6A) with labeled isotype are purchased from Caltag (San Francisco, Calif.). Biotin labeled wheat germ agglutinin (WGA) is purchased from Sigma Chemical Co. (St. Louis, Mo.) and streptavidin red 670A is purchased from Gibco. Standard labeling technique using murine IgG blocker, 30 minute cold incubations and isotypic controls are performed prior to fixation of cells in paraformaldehyde. As a control, binding of biotin labeled WGA is inhibited by a pre-incubated in 2000 fold excess concentration of N-acetyl glucosamine (Sigma) to determine non-lectin-mediated fluorescence. FACS is performed on an EPICS XL scanner (Coulter), selecting separate lymphocyte and nonlymphocyte gated regions for analysis.

Cytokine Analysis: Aliquots of co-culture supernatant are collected at predetermined times and frozen at −70° C. for later analysis. Levels of IFN, IL-4, TGFβ (Genzyme, Cambridge, Mass.) and $PGE_2$ (Cayman Chemical, Ann Arbor, Mich.) are detected by enzyme-linked immunosorbent assays using standard, commercially available kits (murine IFN and IL4, human TGFβ). Bioassays for TNF and IL-6 (L 929 and 7TD cell lines, American Type Culture Collection, Rockville, Md.) are also performed using standard techniques. All studies are performed in triplicate and the results expressed as a mean value.

Immunosuppression and Cardiac Transplantation: Heparinized whole blood is collected from ACI donors and administered fresh to anesthetized Lewis recipients via the penile vein on the day prior to transplantation in the DST control group (1 mL/recipient). Experimental groups received $2.5\times10^6$ viable cultured cells resuspended in 1 ml RPMI/recipient on the day prior to transplants. Heterotopic intra-abdominal ACI to Lewis cardiac transplants are performed using the method of Ono and Lindsey, *J. Thorac. Cardiovasc. Surg* 57:225 (1969). Briefly, the aortic root and pulmonary artery are anastomosed to the recipient infrarenal aorta and vena cava using standard microvascular techniques. Cyclosporine A, a gift of Sandoz Pharmaceuticals (East Hanover, N.J.), is dissolved in olive oil (Sigma) at a concentration of 5 mg/mL and given at a dose of 10 mg/kg subcutaneously the day before transplantation with a daily dose of 2.5 mg/kg for seven days beginning on the day of engraftment. Allograft survival is assessed by daily palpation with rejection defined as a cessation of palpable contractions confirmed under general anesthesia by celiotomy. Graft survival statistics are expressed as a group means i the standard error. Animal groups included untreated, untransfused controls, standard DST controls and experimental groups.

Statistics: Individual in vitro results are compared to baseline using the standard analysis of variance (ANOVA) followed by Tukey's test. Animal group survival data are compared by non-parametric Kruskal-Wallis test followed by pairwise comparisons using the Wilcoxon test. Significance is defined as a p value $\leq 0.05$.

Results

The combinations including GM-CSF and LPS show near complete suppression remain at day seven (and are increased over day four effects). There is no significant increase in suppression when TNF$\alpha$ is added to GM-CSF and LPS. The combination of GM-CSF and LPS is used for the remainder of the in vitro experiments. White cell differentials determined by standard light microscopy with Wright-Giemsa stain show significant numbers of small mononuclear cells and occasional blasts. Clarification of monocyte phenotypes on day seven with double esterase staining show the majority of these cells are macrophages.

Several control groups are done including one receiving no treatment (group 1), a CSA group without DST (group 2), and a standard group given heparinized, whole ACI blood as a DST (group 3). Experimental groups performed include animals receiving infusions of $2.5\times10^6$ (or roughly $7.5\times10^6$ /kg) adherent or nonadherent bone marrow cells cultured with GM-CSF and LPS (groups 4 and 5). Subsequent co-cultures are performed with nonadherent bone marrow cells only; group 6 without LPS and GM-CSF, and group 7 with LPS and GM-CSF. A final group is given an allogeneic co-culture using ACI bone-marrow cells and Lewis splenocytes (group 8). In the absence of treatment, rejection occurs reliably around seven days post-transplantation. Infusion of bone marrow cells cultured without LPS and GM-CSF prove to be inferior to a DST of whole blood (9.3 vs. 16.6 days), but when co-cultured with splenocytes, results are equal to standard DST. Allograft survival in groups 7 and 8 is significantly improved compared to all other groups. Both syngeneic (ACI marrow with ACI spleen) and allogeneic (ACI marrow with Lewis spleen) co-cultures prolonged mean allograft survival past five weeks, with some grafts lasting more than 100 days.

The in-vitro effects of co-cultured cells demonstrate a marked suppression of the MLR and PHA responses in a dose dependent fashion with $1\times10^4$ cells showing significant suppression and near complete suppression noted with the addition of $5\times10^4$ co-culture cells.

To further isolate the suppressor cell population, seven-day co-cultures are then separated on a PERCOLL gradient and the fractions collected. Fractions 3 and 4 are titrated in MLR reactions and have different effects on MLR activity. Fraction 3 shows initiation of significant suppressive effects at the same starting cell concentrations as the whole coculture, while fraction 4 cause significant stimulation characteristic of an active, two-way MLR. The suppressive effects of ACI co-cultures are not strain specific as "third party" MLRs with Buffalo stain stimulators are also suppressed. Suppression of the PHA response by fraction 3 is somewhat more striking in that fewer added cells is required to suppress this response as compared to the MLRs. As noted above, fractions 3 and 4 contain significant numbers of macrophage/monocyte populations. To identify serial changes in co-culture cell phenotypes, FACS analysis of monoclonal cell-surface markers is performed on fractions 3 and 4. Several changes in cell-surface markers are noted in the whole culture, yet fraction 3 cells are rather bland, losing most surface staining characteristics in the non-lymphocyte region. Scatter analysis of fraction 3 shows a mixed population of cells, including a lymphocyte region as well as a distinct population of larger, more granular cells appearing in the macrophage region. This population is less evident in Fr 4. These cells are further sorted by scatter to test the hypothesis that the suppressive cells would be found in the nonlymphocyte (macrophage/monocyte) region.

Sorting of unfixed Fr 3 cells produces $5\times10^5$ macrophage region cells and $7.5\times10^4$ lymphocyte region cells. The nonlymphocyte region cells are tested for their ability to suppress MLRs and demonstrate an increased potency over whole fraction 3 cells with complete suppression at $5\times10^3$ added cells/well, indicating enrichment of the suppressor cells. Wright-Giemsa staining of cells from this region show them to be foamy, granulated macrophages, indicating a high degree of cellular activation.

Early concentrations of IFN are high, but diminish by day 4. Conversely, IL-4 is found in low concentrations initially, but increase substantially over the 7-day culture period. Levels of TGF$\beta$ are also noted to rise over time. Bioassays for TNF show low levels throughout, while IL-6 peaks temporarily around day 4. MLRs performed with 50, 10 or 5FL of added supernatant show stimulation at day 0, and produced suppression at high concentration by day 4, and at all concentrations on day 7.

Alternate Embodiment

The success of a transplant depends on preventing the immune system of the host recipient from recognizing the transplant as foreign and, in some cases, preventing the graft from recognizing the host tissues as foreign. For example, when a host receives a bone marrow transplant, the transplanted bone marrow may recognize the new host as foreign, resulting in graft versus host disease (GVHD). Consequently, the survival of the host depends on preventing both the rejection of the donor bone marrow as well as rejection of the host by the graft immune reaction.

At present, deleterious immune reactions are prevented or treated by general immune suppression in that the suppression is not antigen specific. Nonspecific immune suppression agents, such as steroids and antibodies to lymphocytes, put the host at increased risk for infection and development of tumors. In recent years, unwanted immune reactions have been prevented or treated with more selective immune suppression, such as with Cyclosporine A (CsA). CsA was thought to inhibit the proliferation of cytotoxic T cells while having relatively little effect on the proliferation of suppressor T cells. In addition, immunosuppressive therapy with CsA leads to depletion of the thymic medullary dendritic cells, the principal antigen presenting cells of the adult thymus. Although CsA has significantly improved the overall success of transplants and has shown some success with autoimmune diseases, it must be administered for the life of the patient. As a result, patients receiving such long-term CsA therapy are constantly at considerable risk for infections and neoplasms, as well as toxicity from the CsA.

Unwanted immune reactions which can result in autoimmune disease and transplant rejection can also be inhibited using steroids, azathioprine, anti-T cell antibodies, and more recently, monoclonal antibodies to T cell subpopulations. In addition to CsA, other selective immunosuppressive drugs that have been used include rapamycin, desoxyspergualine, and FK506 (tacrolimus). Unfortunately, when such agents are withdrawn, the unwanted immune reactions often recur. Ideally, it is a primary goal of the methods of the present invention to reduce the amount of general immunosuppressive drugs given to the host. As a result, the tolerant host would remain capable of reacting appropriately to other antigens such as those associated with life-threatening infections or neoplasms.

Therefore, in another embodiment of the present invention, it is possible to separately culture donor specific dendritic cells while, in parallel, culturing suppressor cells in separate media. In this embodiment, dendritic cells and suppressor cells are grown according to methods well known in the art.

Typically, an immunosuppressant agent is administered substantially contemporaneously with the cells. A preferred element of the present invention is that the immunosuppressive agent is administered in only some relatively low dosages.

The method of the invention is useful for preventing an immune reaction to alloantigens (the antigens of an allograft) of transplanted organs from other human donors (allografts). An allograft is a graft to a genetically different member of the same species. Allografts are rejected by virtue of the immunological response of T lymphocytes to histocompatibility antigens. Such tissues for transplant include, but are not limited to, heart, liver, kidney, lung, pancreas, pancreatic islets, brain tissue, cornea, bone, intestine, skin, and hematopoietic cells. The method of the invention is useful in preventing graft versus host disease in cases of mismatched bone marrow or lymphoid tissue transplanted for the treatment of acute leukemia, aplastic anemia, and enzyme or immune deficiencies, for example.

The method of the invention is also useful for treatment of autoimmune diseases where the immune system attacks the host's own tissues. Such autoimmune diseases include, but are not limited to, type 1 insulin-dependent diabetes mellitus, adult respiratory distress syndrome, inflammatory bowel disease, dermatitis, meningitis, thrombotic thrombocytopenic purpura, Sjogren's syndrome, encephalitis, uveitic, leukocyte adhesion deficiency, rheumatoid arthritis, rheumatic fever, Reiter's syndrome, psoriatic arthritis, progressive systemic sclerosis, primary biliary cirrhosis, pemphigus, pemphigoid, necrotizing vasculitis, myasthenia gravis, multiple sclerosis, lupus erythematosus, polymyositis, sarcoidosis, granulomatosis, vasculitis, pernicious anemia, CNS inflammatory disorder, antigen-antibody complex mediated diseases, autoimmune haemolytic anemia, Hashimoto's thyroiditis, Graves disease, habitual spontaneous abortions, Reynard's syndrome, glomerulonephritis, dermatomyositis, chronic active hepatitis, celiac disease, autoimmune complications of AIDS, atrophic gastritis, ankylosing spondylitis and Addison's disease.

In this alternate embodiment, the present invention provides methods of inducing at least partial tolerance to an antigen comprising the steps of administering to the recipient animal a tolerogenic amount of a dendritic cell population; and administering to the recipient animal a tolerogenic amount of a suppressor cell population, substantially contemporaneously with the dendritic cell population. The antigen may be an alloantigen, autoantigen, or xenoantigen.

In yet another embodiment, the present invention includes a method of inducing at least partial tolerance to an antigen comprising the steps of administering to the recipient animal a tolerogenic amount of a dendritic cell population; administering to the recipient animal a tolerogenic amount of a suppressor cell population, substantially contemporaneously with the dendritic cell population; and administering an immunosuppressive agent for a time and under conditions sufficient to induce allograft tolerance wherein the immunosuppressive agent is administered substantially contemporaneously with the administration of dendritic cells and suppressor cells of the present methods. The antigen may be an alloantigen, autoantigen, or xenoantigen.

Suppressor cells are isolated and cultured alone in order to generate natural immunosuppressant cells. The suppressor cells, which may be utilized in the present invention, include any of the cells that act to suppress the action of the host immune system. These include natural suppressor cells ("NSC"), suppressor T-cells ("CD8+" or "T8+"), any suppressor macrophage ("SM"), or any suppressor derived from bone marrow progenitor "immature" cells which are cultured into mature suppressor cells. The CD8+ cells may be isolated from peripheral blood.

Dendritic cells ("DC") may be obtained from one of the sources known in the art by known methods. Typically, the cells are obtained from the bone marrow, blood, liver, fetal liver, or the spleen or may be obtained by differentiating bone marrow progenitor cells.

The methods of the present invention may use bone marrow cells obtained from iliac crest, femora, tibiae, spine, rib or other medullary spaces. Alternatively, the methods could use stem cells from other sources of human stem cells, e.g., from embryonic yolk sac, placenta, umbilical cord, fetal and adolescent skin, and blood.

These cells can be subsequently administered as a form of pre-transplant or post-transplant DST. When given as a DST on the day prior to transplantation, the treatment results in a marked prolongation of allograft survival.

The fractionation of both cell cultures and transplant cellular sources can isolate and enrich subpopulations of cells that retain the properties of suppressor cell function and equally prolong allograft survival. The suppressor cells may be concentrated by PERCOLL fractionation and further enriched by FACS sorting.

One or more of the hormones selected from the group consisting of GM-CSF, cytokines, interleukins (e.g., IL-2, IL-3, IL-4, IL-6), TNF, and LPS may be added as part of the culture conditions.

A "cytokine" is any one of the groups of hormone-like mediators produced by lymphocytes. Representative cytokines include but are not limited to IL1, IL2, IL3, IL4, IL6 and gamma IFN. The term cytokine is generally accepted to extend to other trophic factors that share biological functions and/or receptor signaling properties with lymphocyte-derived mediators.

As used herein, "an effective amount" or "tolerogenic amount" of the therapeutic cells is that the number of cells administered which includes enough cells to be capable of inducing at least partial tolerance to an alloantigen in a host animal. As used herein, "a safe and effective amount" of the therapeutic cells is pharmaceutically safe to a subject and that amount includes enough cells to cause an increase in allograft survival while causing no side effects or an acceptable level of side effects.

Therapeutic cells of the present invention are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals and growth factors. The pH of the medium is preferably maintained at a pH greater than about two and less than about eight, preferably at about pH 6.5. Methods for maintaining a stable pH include buffering and constant pH control, preferably through the addition of sodium hydroxide. Preferred buffering agents include succinic acid and Bis-Tris (Sigma Chemical Co., St. Louis, Mo.). Cultured mammalian cells are generally grown in commercially available serum-containing or serum-free media. Selection of a medium appropriate for the particular cell line used is within the level of ordinary skill in the art.

The nutrient medium can contain, as elemental components, sodium, potassium, calcium, magnesium, phosphorus, chlorine, amino acid(s), vitamin(s), hormone (s), antibiotics, serum, or other chemical components depending on application purposes. The nutrient medium can contain a cytokine such as interleukin-1, interleukin-2, interleukin-3, interleukin-4, interleukin-5, interleukin-6, interleukin-7, interleukin-8, interleukin-9, interleukin-10, interleukin-11, interleukin-12, TNF (Tumor Necrosis Factor), gamma—interferon, a granulocyte macrophage colony-stimulating factor (GM-CSF), a granulocyte colony-stimulating factor (G-CSF), or a macrophage colony-stimulating factor (M-CSF), depending on application purposes.

The two separate cell cultures (dendritic cells and suppressor cells) may be propagated for about 1 day to about 21 days and are preferably propagated from about 2 days to about 10 days and most preferably for about 7 days. Typically, the cells will be propagated for about the same length of time. However, one type could be grown for a different length of time. At the end of the propagation phase, the dendritic and suppressor cells are recovered and delivered to a host.

Introduction into Host

It is contemplated that target cells will be located within an animal or human patient, in which case a safe and effective amount of the therapeutic cells, in pharmacologically acceptable form, would be administered to the patient. Generally speaking, it is contemplated that useful methods of the present invention will include the selected cells in a convenient amount, e.g., from about $1 \times 10^6$ total cells/kg body weight to about $1 \times 10^9$ total cells/kg body weight of the dendritic and suppressor cell mix, administered at a dosage of about $1 \times 10^5$ total cells/kg body weight to about $1 \times 10^8$ total cells/kg body weight of the dendritic and suppressor cell mix.

Typically, the two populations of cells will be mixed prior to administration to a host but may be administered separately to the host. The cells are preferably administered in a ratio from about 2:1 to about 1:20 dendritic cells:suppressor cells. The cells are more preferably administered in a ratio of from about 1:1 to about 1:10 dendritic cells:suppressor cells.

Alternatively, the two populations may be administered separately over a course of about 1 day to about 14 days.

Typically, the cells are diluted in a pharmacologically or physiologically acceptable carrier, such as, for example, phosphate buffered saline. The route of administration and ultimate amounts of material that is administered to the patient or animal under such circumstances will depend upon the intended application and will be apparent to those of skill in the art in light of the factors which follow.

The therapeutic cells can comprise, in addition to the cells, compounds and/or compositions that will also aid in relief of the symptoms of a target disease, such as immunosuppressant drugs, native hormones, adjuvant compounds or complementary drugs and hormones, in dosages useful for relief of the symptoms of the particular disease, as known to those skilled in the art. Dosages for the above-mentioned additional compounds are established and known to those skilled in the art. The ratio of therapeutic cells to additional agents is dependent upon the dose desired of each individual compound. Preferably, the additional agent will be administered as a pharmaceutically acceptable solution.

The compound useful in the present inventive method may be administered by any suitable means. One skilled in the art will appreciate that many suitable methods of administering the compound to an animal in the context of the present invention, in particular a human, are available, and, although more than one route may be used to administer a particular compound, a particular route of administration may provide a more immediate and more effective reaction than another route.

The cells should be administered such that a therapeutical number resides in the body. The number of cells administered to an animal, particularly a human, in the context of the present invention should be sufficient to effect a therapeutic response in the animal over a reasonable period of time.

The cells may be administered in a pharmaceutically acceptable carrier. Pharmaceutically acceptable carriers are well known to those who are skilled in the art. The choice of carriers will be determined in part by the kind and number of cells delivered, as well as by the particular method used to administer the composition. Accordingly, there are a wide variety of suitable formulations of the pharmaceutical composition of the present invention.

Formulations suitable for intravenous and intraperitoneal administration, for example, include aqueous and nonaqueous, isotonic sterile injection solutions, which can contain anti-oxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives.

The exact amount of such compounds required will vary from subject to subject, depending on the species, age, and general condition of the subject, the severity of the disease that is being treated, the particular compound used, its mode of administration, and the like. Since the cells may be administered intravenously, intra-arterially, or peritoneally, the choice will be determined by such factors as the location of the target site(s) within the body. The dosage will vary according to such factors as degree of compatibility of the donor and recipient, the health of the host, and the amount of immunosuppressant drugs given concurrently. Thus, it is not possible to specify an exact activity-promoting amount. However, an appropriate amount may be determined by one of ordinary skill in the art using only routine testing given the teachings herein.

Typically, nonspecific immunosuppressive agents are administered in conjunction with the administration of the two cell populations. Such agents include cyclosporine ("CSA"); typically administered in about 6 mg/kg body weight ("BW") to about 10 mg/kg BW initial dose), methotrexate, desoxyspergualine, rapamycin, steroids (e.g., prednisone), SOLUMEDROI (about 250 mg/kg BW to about 1000 mg/kg BW), ATGAM, OKT3, N-monomethylformamide (MMF), azathioprine (known in the industry as IMURAN) and FK506.

The methods of the invention also comprise administering, to a host, an enriched dendritic cell population in combination with an enriched suppressor cell population suspended in a pharmaceutically-acceptable carrier.

As used herein, the term "enriched" as applied to the cell populations of the invention refers to a more homogeneous population of dendritic or suppressor cells which have fewer other cells with which they are naturally associated. An enriched population of cells can be achieved by several methods known in the art. For example, an enriched population of dendritic cells can be obtained using immunoaffinity chromatography using monoclonal antibodies specific for determinants found only on dendritic cells.

Enriched populations can also be obtained from mixed cell suspensions by positive selection (collecting only the desired cells) or negative selection (removing the undesirable cells). The technology for capturing specific cells on affinity materials is well known in the art (Wigzel, et al., J. Exp. Med., 128:23, 1969; Mage, et al., J. Imnmunol. Meth., 15:47, 1977; Wysocki, et al., Proc. Natl. Acad. Sci. U.S.A., 75:2844, 1978; Schrempf-Decker, et al., J. Immunol Meth., 32:285, 1980; Muller-Sieburg, et al., Cell, 44:653, 1986).

Monoclonal antibodies against antigens specific for mature, differentiated cells have been used in a variety of negative selection strategies to remove undesired cells, for example, to deplete T cells or malignant cells from allogeneic or autologous marrow grafts, respectively (Gee, et al., J.N.C.I. 80:154, 1988). Purification of human hematopoietic cells by negative selection with monoclonal antibodies and immunomagnetic microspheres can be accomplished using multiple monoclonal antibodies (Griffin, et al., Blood, 63:904, 1984). Enriched dendritic cell composition can be obtained from a mixture of lymphocytes, since dendritic cells lack surface Ig or T cell markers and do not respond to B or T cell mitogens in vitro. Dendritic cells also fail to react with MAC-1 monoclonal antibodies, which reacts with all macrophages. Therefore, MAC-1 antibodies provide a means of negative selection for dendritic cells.

Procedures for separation of cells may include magnetic separation, using antibodycoated magnetic beads, affinity chromatography, cytotoxic agents joined to a monoclonal antibody or used in conjunction with a monoclonal antibody, for example, complement and cytotoxins, and "panning" with antibodies attached to a solid matrix, for example, plate, or other convenient technique. Techniques providing accurate separation include fluorescence activated cell sorters, which can have varying degrees of sophistication, for example, a plurality of color channels, low angle and obtuse light scattering detecting channels, impedance channels, etc.

The immunosuppressive agent used according to the method of the invention is an agent that decreases the host's immune response to antigens. A preferred immunosuppressant of the invention is Cyclosporine A (CsA), however other agents, which cause immune suppression by depletion of thymic medulla dendritic cells, such as rapamycin, desoxyspergualine, and FK506 or functional equivalents of these compounds, may also be utilized. CsA is preferably administered by injection at a dose from about 0.3 to about 50 mg/kg/day, preferably from about 2.5 mg/kg/day to about 10 mg/kg/day. The duration of CsA treatment may range from about two to about 20 days, preferably about 14 days.

The immunosuppressive agent is administered by any suitable means, including parenteral, subcutaneous, intrapulmonary, and intranasal administration, and if desired for local immunosuppressive treatment, intralesional administration (including perfusing or otherwise contacting the graft with the immunosuppressive agent prior to transplantation). Parenteral infusions include intramuscular, intravenous, intraarterial, or intraperitoneal administration. In addition, the immunosuppressive agent is suitably administered by pulse infusion, particularly with declining doses of the immunosuppressive agent. Preferably, the dosing is given by injections, most preferably intravenous or subcutaneous injections, depending in part on whether the administration is brief or chronic.

As used herein, "substantially contemporaneously" refers to the time at which each of the therapeutic cells or immunosuppressant is administered to the recipient in relation to the time at which the others are administered. For example, a heart transplant recipient may receive enriched dendritic cells derived from donor spleen, during transplant surgery and receive CsA for a short time immediately following for about 10–16 days, preferably about 14 days. In general, where transplant grafts are involved, the immunosuppressive agent can be administered from about one day to about 90 days before infusion of the tolerogenic cells until about seven days to about 90 days after the infusion of tolerogenic cells. Preferably, the immunosuppressive agent is administered from about seven days to about 28 days before infusion of tolerogenic cells until about seven days to about 28 days after infusion of tolerogenic cells. Where autoimmune disease is treated by infusion of foreign or altered tolerogenic cells, administration of immunosuppressive agent parallels the treatment times described for transplant grafts.

According to the invention, an allogeneic bone marrow transplant recipient may have his own bone marrow harvested and processed to obtain a composition of enriched dendritic cells before transplantation of the donor bone marrow. The patient may receive immunosuppressive therapy followed by the infusion of transplanted bone marrow and dendritic cell composition previously harvested from the patient's own bone marrow.

Enriched cells are administered in a physiologically acceptable solution. Preparations of enriched tolerogenic cells for parenteral administration include sterile aqueous or nonaqueous solutions, suspensions, and emulsions. Nonaqueous solvents include propylene glycol, and polyethylene glycol. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, and inert gases and the like.

In an additional aspect, the present invention is directed to various methods of utilizing the cell mix produced by the present invention for therapeutic and/or diagnostic purposes. For example, the mix of dendritic cells and suppressor cells may find use in: (1) regenerating tissues which have been damaged through acute injury, abnormal genetic expression or acquired disease; (2) treating a host with damaged tissue by removal of small aliquots of bone marrow, differentiating them in vitro, isolating the desired subpopulation of differentiated cells and re-introducing the differentiated cells back into the host (3) detecting and evaluating growth factors relevant to the immune system; (4) detecting and evaluating inhibitory factors which modulate the immune system.

Bone Marrow Preparation. Whole, unfractionated bone marrow is typically obtained from rib or long bones by flushing with Hank's Balanced Salt Solution ("HBSS"), or vertebral body bone marrow obtained by crushing with a bone rongeurs and elution with buffer solution, is filtered through nylon mesh and the viability assessed by trypan blue exclusion using a hemocytometer. The cells are collected by centrifugation at 1400 rpm for five minutes and then lysed with 25 mL of sterile, distilled water followed immediately by 25 mL of double strength HBSS. Cells are then recollected by centrifugation and pooled into one conical tube using a horizontal pipetting technique to exclude agglutinated material. Cells are resuspended in Roswell Park Memorial Institute Media ("RPMI") at a concentration of $1-2 \times 10^6$ large mononuclear cells /mL and incubated at 37° C. in 5% $CO_2$ for one hour (to adhere cells). The nonadherent cells are collected and washed in HBSS and the viability rechecked. Cells are stored at 4° C. until used.

Splenocyte Preparation. Typically, splenic tissue is cut into small (approximately 0.5–1 GM) pieces and crushed using any convenient method (between glass slides or using a scraping technique with a sterile disposable blade), and collected in HBSS. The tissue is filtered through nylon mesh and collected by centrifugation. The cells are pooled and resuspended in 15 mL of HBSS, beneath which is layered 7.5 mL of FICOLL-HYPAQUE. This gradient is centrifuged at 1000 rpm for 45 minutes (no brake) and the interface cells collected and pooled. The pellet and solution are discarded. The pooled cells are washed three times in HBSS and resuspended in RPMI, and viability and cell counts checked. Cells are stored at 4° C. until used.

Culture Set-Up. Splenocytes and bone marrow cells are separately suspended in RPMI or similar medium to a concentration of about $2 \times 10^6$ cells/mL. The media is supplemented with the appropriate growth factor or stimulant and incubated at 37° C. in 5% $CO_2$ (minimum but not to exceed 10%) at a concentration of $3.3 \times 10^5$ cells/square cm floor surface. Cultures are maintained using standard humidity, for at least 4 days (and up to 14 days) undisturbed and unshaken.

Supplemental Factors: Specific supplementation with colony stimulating factors is necessary. The current technique utilizes species specific granulocyte macrophage-colony stimulating factor (GM-CSF). Where species specific factor is unavailable (i.e. the rat) murine GM-CSF is used and a concentration of 100 units/mL is added at the start of the culture. Additional agents for the stimulation and maturation of cells are added. The current model employs lipopolysaccharide (LPS or bacterial endotoxin) obtained from E coli and added at 1 µg/mL at the start of the culture. Additional growth/factors that may be used in addition or in place of GM-CSF include macrophage colony stimulating factor ("M-CSF"), granulocyte-colony stimulating factor ("G-CSF") and the FLT3 ligand. Additional stimulating factors that may be added or used in place of LPS include interleukin-6, interleukin-4, tumor necrosis factor alpha ("TNFα"), and transforming growth factor beta ("TGFβ"). Again, all factors used are species specific unless unavailable, in which case either murine or human factors can be employed.

Cell Harvest. Typically, cells are harvested and pooled by first obtaining nonadherent cells and rinsing the culture container and collecting the cells and washes in separate tubes. Following centrifugation, supernatants may be saved or frozen for analysis. The cells are resuspended and counted and their viability checked using trypan blue exclusion. Cells may be used unfractionated or following a number of fractionation techniques. The current method employs the use of unfractionated cells resuspended in sterile, pH-balanced medium. For fractionation, a discontinuous PERCOLL gradient is used with a 100%, 70%, 60%, 50%, 40% and 0% stepwise dilution. The cells are suspended in 100% PERCOLL and equal volumes of diluted PERCOLL are layered sequentially above the cells. The gradient is harvested after centrifugation at 1000 g (2300 rpm) for 60 minutes. Cells are obtained separately at each interface, counted, and the viability checked.

EXAMPLES

Culture Technique: Fresh spleens and lower extremity long bones are harvested aseptically and kept on ice in Hank's balanced salt solution (HBSS, Gibco Life Technologies, Gaithersburg Md.). Spleens are crushed between glass slides and sterile, filtered, splenic tissue is washed in HBSS, centrifuged on a FICOLL-HYPAQUE (HISTOPAQUE 1077, Sigma Diagnostics, St. Louis, Mo.) gradient at 1000 RPM×45 min. and the white cell layer harvested, washed twice, resuspended in Roswell Park Memorial Institute (RPMI) medium (Gibco) with 10% fetal calf serum (FCS) (Hyclone Labs, Logan, UT) and 100 units/mL penicillin, 100 µg/mL streptomycin sulfate, and 0.25 µg/mL amphotericin B (Gibco), to $2 \times 10^6$ cells/ml. Bone marrow harvests are performed as previously described by Ogle et al., *Inflammation* 18:175 (1994). The marrow cells are resuspended in RPMI+10% FCS, counted and diluted to $1 \times 10^6$ large, mononuclear cells/ml. Twenty-five mL aliquots are incubated for 60 min. at 37° C. and 5% $CO_2$ in 250 mL, 75 $cm^2$ sterile, vented culture flasks (Costar, Cambridge Mass.). Nonadherent cells are then collected, washed and resuspended to $2 \times 10^6$ cells/mL. Co-cultures consisted of equal volumes of spleen and marrow cells (total $1 \times 10^6$ of each cell stock/mL), most with added LPS (1 µg/mL, *E. coli* 055:B5, Sigma Chemical, St. Louis, Mo.) and murine GM-CSF (100 units/mL, R and D Systems, Minneapolis, Minn.) and are incubated for up to 7 days at 37° C. and 5% $CO_2$ in 25 ml volumes in 250 mL sterile culture flasks. All cell counts are based on viable cells by trypan blue exclusion. Nonadherent co-culture cells are harvested at predetermined times, washed, resuspended and counted.

Some initial cultures using nonadherent bone marrow only are performed with various combinations of LPS, murine GM-CSF, recombinant human TNFα (100 units/ml, Endogen, Boston Mass.) or unmodified media and harvested at day 4 or 7 and used in mixed lymphocyte and phytohemagglutinin (PHA, Sigma, St. Louis, Mo.) experiments.

Cell fractionation: Cells are washed twice in HBSS, pelleted in a 15-ml conical tube at 1400 RPM×5 min. and resuspended to 2 ml in PERCOLL (Pharmacia, Uppsala, Sweden) solution (0.95 ml 10× HBSS in 9.05 ml sterile 100% PERCOLL, pH titrated to 7.35) over which are layered 2 ml each of 70%, 60%, 50%, 40% and 0% (plain HBSS) PERCOLL dilutions. After centrifugation at 2800 RPM×30 min., fractions at gradient interfaces are retrieved, washed and resuspended in RPMI with 10% FCS. Fractions (Fr) are labeled sequentially from the 100–70% interface (Fr 1) to the 40–0% interface (Fr 5). The fractionation of untreated bone marrow yielded 4 fractions (lacking cells at the 50–40% interface), while 7-day co-cultures yielded 5 fractions. Fraction 5 contained 97% dead cells, while Frs 1 and 2 contained very few but mostly viable cells (these are submitted for FACS analysis). Fraction 3 contained the majority of total cells (66%) at 95% viability, while Fr 4 contained somewhat fewer cells at similar viability (Frs 3 and 4 are used in further experiments). Subsequent separation of Fr 3 cells is accomplished by sterile, viable cell sorting on an Epics 753 cell sorter (Coulter, Miami Fla.) into subpopulations based on scatter pattern (debris, lymphocyte, and macrophage regions). Averages of 60% of cells are lost during sorting. This is attributed to fragility acquired by some cells over time in culture. Macrophage region cells are used in further experiments.

Mixed Lymphocyte Reactions: Spleens are harvested aseptically, crushed, filtered and washed in HBSS, then resuspended in 15 ml HBSS and separated on a FICOLL-HYPAQUE gradient at 1000 RPM×45 min. The white cells are harvested, washed, resuspended in RPMI with 10% FCS and cells incubated with 25Fg Mitomycin C. (Sigma, St. Louis, Mo.)/$2.5\times10^7$ cells/mL for 45 minutes at 37° C. and 5% $CO_2$ then washed 3× in RPMI are used as stimulator cells. Responder and stimulator cells are added to standard 96 well culture plates at $2.0\times10^6$ cells/well to which are added titrations of whole co-culture, fr 3, or fr 4 cells or titrated amounts of co-culture supernatant. Cells are pulsed with 0.5 FCi/well of $^3$H-thymidine (1 mCi/mL New England Nuclear, Boston, Mass.) and harvested on day 4. Activity is measured as counts per minute (cpm) with an LS600TA liquid scintillation counter (Beckman, Fullerton, Calif.). All reactions are performed in triplicate and results expressed as mean values.

Immunosuppression and Cardiac Transplantation: Heparinized whole blood is collected from ACI donors and administered fresh to anesthetized Lewis recipients via the penile vein on the day prior to transplantation in the DST control group (1 mL/recipient). Experimental groups received $2.5\times10^6$ viable cultured cells resuspended in 1 ml RPMI/recipient on the day prior to transplants. Heterotopic intra-abdominal ACI to Lewis cardiac transplants are performed using the method of Ono and Lindsey, *J. Thorac. Cardiovasc. Surg.* 57:225 (1969). Briefly, the aortic root and pulmonary artery are anastomosed to the recipient infrarenal aorta and vena cava using standard microvascular techniques. Cyclosporine A, a gift of Sandoz Pharmaceuticals (East Hanover, N.J.), is dissolved in olive oil (Sigma) at a concentration of 5 mg/mL and given at a dose of 10 mg/kg subcutaneously the day before transplantation with a daily dose of 2.5 mg/kg for seven days beginning on the day of engraftment. Allograft survival is assessed by daily palpation with rejection defined as a cessation of palpable contractions confirmed under general anesthesia by celiotomy. Graft survival statistics are expressed as a group means±the standard error. Animal groups included untreated, untransfused controls, standard DST controls and experimental groups.

In one embodiment of the invention a process for differentiating stem cells comprises providing a stem cell specimen, combining the stem cell specimen with a second cell specimen to produce a co-culture, and adding factors to the co-culture. The co-cultures are maintained for from about 4 days to about 14 days.

Additional embodiments and modifications within the scope of the claimed invention will be apparent to one of ordinary skill in the art. Accordingly, the scope of the present invention will be considered in the terms of the following claims, and is understood not to be limited to the details of the methods described in the specification.

We claim:

1. A method of treatment comprising the steps of:
   (a) obtaining stem cells from bone marrow;
   (b) combining the stem cells with splenocytes to form a co-culture;
   (c) adding a first factor selected from the group consisting of lipopolysaccharide, interleukin-6, interleukin-4, tumor necrosis factor alpha, transforming growth factor beta, anti-CD3 and mixtures thereof to the co-culture;
   (d) adding a second factor selected from the group consisting of granulocyte macrophage colony-stimulating factor, macrophage-colony stimulating factor, granulocyte-colony stimulating factor, FLT3 ligand and mixtures thereof to the co-culture;
   (e) maintaining the co-culture for at least 4 days;
   (f) obtaining differentiated immune system suppressor cells and immune system stimulator cells from the co-culture; and
   (g) introducing the immune system suppressor cells and immune system stimulatory cells into a host;
   wherein the immune system suppressor cells are capable of prolonging allograft survival when infused as a donor specific transfusion to a transplant patient.

2. A method according to claim 1, wherein the immune system stimulatory cells and immune system suppressor cells are introduced to the host as a donor specific transfusion one day prior to transplant.

3. A method according to claim 1, wherein the immune system stimulatory cells and immune system suppressor cells are introduced to the host as multiple donor specific transfusions after transplant.

4. A method according to claim 1, wherein the co-culture is maintained for from 4 to 14 days.

5. A method according to claim 1, wherein the host received a course of cyclosporine at a dose of from about 0.3 to about 50 mg/Kg/day for from about 2 to about 20 days.

6. A method according to claim 5, wherein the course of cyclosporine is for 8 days.

7. A method according to claim 4, wherein the stem cells and splenocytes are co-cultured in a medium comprising 100 units/ml granulocyte macrophage-colony stimulating factor and 1 µg/ml lipopolysaccharide.

8. A method according to claim 5, wherein the immune system stimulator cells and immune system suppressor cells are introduced into the host in an amount of less than $1\times10^7$ total cells/kg host body weight.

9. A method according to claim 7, wherein the immune system suppressor cell is a macrophage.

10. A method of reducing the amounts of general immunosuppressive drugs given to a transplant patient, comprising the steps of:
    a) removing bone marrow;
    b) obtaining a first population of cells from the bone marrow, wherein the first population of cells are stem cells;
    c) combining the stem cells with a second cell population derived from lymphoid tissue to produce a co-culture;
    d) adding granulocyte macrophage-colony stimulating factor and lipopolysaccharide to the co-culture;
    e) allowing the stem cells to differentiate;
    f) obtaining immune system suppressor cells from the co-culture;
    g) administering to a transplant patient the immune system suppressor cells and a third population of cells, wherein the third population of cells are dendritic cells selected from the group consisting of dendritic cells of splenic, bone marrow, blood, liver and fetal liver origin, and mixtures thereof;
    wherein the immune system suppressor cells are capable of prolonging graft survival in the transplant patient.

11. A method according to claim 10, wherein the immune system suppressor cells and the dendritic cells are administered to a transplant patient as a donor specific transfusion in a dendritic cell:suppressor cell ratio of from about 2:1 to about 1:20.

12. A method according to claim 10, wherein the transplant patient further receives cyclosporine for a period of time starting from about 1 to about 90 days before receiving the cells and ending from about 7 to about 90 days after receiving the cells.

13. A method according to claim 10, wherein the dendritic cells are derived from spleen cells.

14. A method according to claim 10, wherein the transplant patient receives immune system suppressor cells and dendritic cells in an amount of from about $1 \times 10^6$ to about $1 \times 10^9$ total cells per kilogram body weight.

15. A method according to claim 12, wherein an immunospressive agent is administered to the transplant patient.

16. A method according to claim 13, wherein the co-culture is maintained for from 4 to 14 days, and wherein medium used for the co-culture comprises 100 units/ml granulocyte macrophage-colony stimulating factor and 1 $\mu$g/ml lipopolysaccharide.

17. A method of treatment comprising the steps of:
a) obtaining stem cells from bone marrow;
b) combining the stem cells with splenocytes in medium to form a co-culture;
c) adding to the medium granulocyte macrophage-colony stimulating factor at a level of 100 units/ml medium, and lipopolysaccharide at a level of 1 $\mu$g/ml medium;
d) maintaining the co-culture for from 4 to 14 days;
e) obtaining differentiated immune system suppressor cells from the co-culture;
f) introducing the immune system suppressor cells into a host; and
g) substantially contemporaneously introducing an enriched population splenic of dendritic cells into the host;
wherein the immune system suppressor cells are capable of prolonging allograft survival when infused as a donor specific transfusion to a transplant patient.

18. A method according to claim 17, wherein the immune system suppressor cells and the splenic dendritic cells are administered to the host in a ratio of from about 2:1 to about 1:20.

19. A method according to claim 18, wherein the host receives from about 2.5 to about 10 mg/Kg body weight/day of cyclosporine A for from about 2 to about 20 days.

20. A method according to claim 19, wherein the host receives of a total of immune system suppressor cells and splenic dendritic cells of from about $1 \times 10^6$ to $10 \times 10^9$ total cells/Kg body weight.

* * * * *

UNITED STATES PATENT AND TRADEMARK OFFICE
CERTIFICATE OF CORRECTION

PATENT NO. : 6,165,785
DATED : December 26, 2000
INVENTOR(S) : Cora K. Ogle, John F. Valente, J. Wesley Alexander It is certified that error appears in the above-identified patent and that said Letters Patent is hereby corrected as shown below:

In claim 8, line 1, the "5" should be --6--.
In claim 17, the second line of subpart (g) should read "enriched dendritic cells."

Signed and Sealed this

Twenty-ninth Day of May, 2001

*Attest:*

NICHOLAS P. GODICI

*Attesting Officer*     *Acting Director of the United States Patent and Trademark Office*